(12) United States Patent  
Grace

(10) Patent No.: US 10,820,943 B2  
(45) Date of Patent: Nov. 3, 2020

(54) LASER GENERATOR USING DIFFRACTIVE OPTICAL ELEMENT

(71) Applicant: KONINKLIJKE PHILIPS N.V., Eindhoven (NL)

(72) Inventor: Kenneth P. Grace, Woodland Park, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 213 days.

(21) Appl. No.: 16/035,557

(22) Filed: Jul. 13, 2018

(65) Prior Publication Data

US 2019/0015157 A1  Jan. 17, 2019

Related U.S. Application Data

(60) Provisional application No. 62/614,234, filed on Jan. 5, 2018, provisional application No. 62/532,286, filed on Jul. 13, 2017.

(51) Int. Cl.
| | |
|---|---|
| A61B 18/20 | (2006.01) |
| A61B 18/24 | (2006.01) |
| G02B 6/42 | (2006.01) |
| G02B 6/06 | (2006.01) |
| G02B 5/02 | (2006.01) |
| G02B 27/09 | (2006.01) |
| G02B 27/28 | (2006.01) |
| H01S 3/00 | (2006.01) |
| A61B 18/00 | (2006.01) |
| A61B 18/22 | (2006.01) |

(52) U.S. Cl.
CPC ............ *A61B 18/245* (2013.01); *A61B 18/20* (2013.01); *G02B 5/0252* (2013.01); *G02B 6/06* (2013.01); *G02B 6/4286* (2013.01); *G02B 6/4296* (2013.01); *G02B 27/0961* (2013.01); *G02B 27/283* (2013.01); *H01S 3/005* (2013.01); *A61B 2018/00386* (2013.01); *A61B 2018/00422* (2013.01); *A61B 2018/2211* (2013.01); *A61B 2018/2261* (2013.01)

(58) Field of Classification Search
CPC ...... G02B 6/06; G02B 6/4296; G02B 27/283; G02B 27/0961; G02B 6/4286; G02B 5/0252; H01S 3/005; A61B 18/245; A61B 2018/00386; A61B 2018/2261; A61B 2018/2211; A61B 2018/00422
See application file for complete search history.

(56) References Cited

U.S. PATENT DOCUMENTS

| 5,315,614 | A | 5/1994 | Grace et al. |
| 7,050,692 | B2 | 5/2006 | Harlan et al. |
| 8,059,274 | B2 | 11/2011 | Splinter |

OTHER PUBLICATIONS

Tianheng Wang, et al, Application of laser pulse stretching scheme for efficiently delivering laser energy in photoacoustic imaging, Journal of Biomedical Optics 17(6), 061218-1 to 061218-8 (Jun. 2012).

(Continued)

*Primary Examiner* — Rex R Holmes

(57) ABSTRACT

The present disclosure relates generally to devices, methods and systems for laser generators, and more specifically, to laser generators having an optical assembly, which allows fiber optic catheters to couple to laser generators while delivering laser beams.

14 Claims, 11 Drawing Sheets

(3 of 11 Drawing Sheet(s) Filed in Color)

(56) References Cited

OTHER PUBLICATIONS

Rajeev Khare and Paritosh K. Shukla, Ch. 10—Temporal Stretching of Laser Pulses, Coherence and Ultrashort Pulse Laser Emission, Coherence and Ultrashort Pulse Laser Emission (Nov. 2010).
Amir Herzog, et al, Effect of spatial coherence on damage occurrence in multimode optical fibers, p. 415, Feb. 1, 2015 / vol. 40, No. 3 / Optics Letters.

LASER GENERATOR USING DIFFRACTIVE OPTICAL ELEMENT

CROSS-REFERENCE TO RELATED APPLICATION

The present application claims the benefit of and priority to, under 35 U.S.C. § 119 and/or 35 U.S.C. § 120, U.S. Provisional Application Ser. No. 62/614,234, filed Jan. 5, 2018, entitled LASER GENERATOR USING DIFFRACTIVE OPTICAL ELEMENT and U.S. Provisional Application Ser. No. 62/532,286, filed Jul. 13, 2017, entitled METHODS OF PERFORMING TISSUE ABLATION USING DIFFERING WAVELENGTHS, both of which are hereby incorporated by reference in its entirety for all purposes.

FIELD OF THE DISCLOSURE

The present disclosure relates generally to devices, methods and systems for laser generators, and more specifically, to laser generators having an optical assembly, which allows fiber optic catheters to couple to laser generators while delivering laser beams.

BACKGROUND

When performing a laser atherectomy procedure in a patient's vasculature and utilizing a disposable fiber optic catheter, the catheter is typically coupled to a laser generator, such as the CVX-300™ excimer laser system, which is manufactured by The Spectranetics Corporation, Colorado Springs, Colo., USA. Different laser generators generally produce different laser beams. The CVX-300™ excimer laser system produces a 308 nanometer laser beam with a pulse width of approximately 135 nano seconds (nsec). Other laser systems may produce a laser beam having a different wavelength and pulse width. For example, a Nd:YAG laser operating at its third harmonic produces a 355 nanometer laser beam with a pulse width of approximately 8 nsec. The 308 nanometer laser beam having pulse width of approximately 135 nsec may be capable of producing maximum energy output of 140 milli-joules (mJ), and the 355 nanometer laser beam having a pulse width of approximately 8 nsec may be capable of producing maximum energy output of 200 milli-joules (mJ). But the optical fibers in the laser catheter that are used to deliver the energy are potentially subject to failure if the amount of energy in a pulse exceeds a certain threshold. The likelihood of such failure is increased if the laser beam inherently has a greater peak power. For example, due to the relatively short duration (e.g., 8 nsec) of the puke width of the 355 nanometer laser beam in comparison to the 308 nanometer laser beam, which has a puke width of 135 nsec, the 355 nanometer laser beam must have a substantially higher peak power for a given puke because the puke width of the 355 nanometer beam k over sixteen times shorter than the length of the puke width of the 308 nanometer beam. Accordingly, there is a need to increase the pulse width of a laser beam in order to decrease the peak power of the energy traveling through the optical fibers in order to prevent the power level from exceeding the damage threshold of the fiber optic delivery device. Moreover, regardless of the wavelength of the laser beam, a need may exist to improve the symmetry and homogeneity of the intensity of the laser beam exiting the laser system and/or the disposable fiber optic catheter so as to further decrease the likely of damaging the optical fibers.

SUMMARY

The devices of the present disclosure increase the puke width of a laser beam and decrease the peak power of the energy traveling through the optical fibers, thereby minimizing and/or preventing the power level from exceeding the damage threshold of the fiber optic delivery device. Moreover, the devices of the present disclosure improve the symmetry and homogeneity of the intensity of the laser beam exiting the laser system and/or the disposable fiber optic catheter so as to further decrease the likely of damaging the optical fibers.

A device for performing intravascular ablation includes a laser generator comprising a laser source producing a beam of light and an optical assembly downstream of the laser source, wherein the optical assembly receives the beam of light, wherein the optical assembly comprises a waveplate receiving the beam of light, a thin film polarizer downstream of the waveplate and receiving the beam of light and reflecting a first portion of the beam and allowing a second portion of the beam to pass there through, a beam dump receiving the first portion of the beam, a beam expander downstream of the waveplate and receiving the second portion of the beam, a diffuser downstream of the beam expander and receiving the second portion of the beam of light, and a mixing fiber downstream of the diffuser and receiving the second portion of the beam of light, wherein the mixing fiber emits the second portion of the beam of light.

The laser generator of the preceding paragraph, wherein the laser source produces a beam of light comprising about 355 nanometers The laser generator of any of the preceding paragraphs, wherein the laser source produces a beam of light between about 10 nanometers to about 5000 nanometers.

The laser generator of any of the preceding paragraphs, wherein the diffuser is a diffracting optical element.

Another device for performing intravascular ablation includes a laser generator comprising a laser source producing a beam of light having a plurality of pulses, wherein the pulses comprise a pulse width, and an optical assembly downstream of the laser source, wherein the optical assembly receives the beam of light, wherein the optical assembly comprises a waveplate receiving the beam of light, a thin film polarizer downstream of the waveplate and receiving the beam of light and reflecting a first portion of the beam and allowing a second portion of the beam to pass there through, wherein the second portion of the beam has the pulse width, a beam dump receiving the first portion of the beam, a means for stretching the pulse width of at least one of the plurality of pulses in the second portion of the beam, and a diffuser downstream of the means for stretching the pulse width and receiving and emitting the other portion of the second beam.

The laser generator of the preceding paragraph, wherein the means for stretching the width of at least one of the plurality of pulses comprises a beam splitter and a plurality of mirrors creating a beam path.

The laser generator of any of the preceding paragraphs, wherein at least one of the mirrors is capable of translating.

The laser generator of any of the preceding paragraphs, wherein the means for stretching the width of at least one of the plurality of pulses comprises beam splitter.

The laser generator of any of the preceding paragraphs, wherein the beam splitter spots the second portion of the beam into a first beam and a second beam.

The laser generator of any of the preceding paragraphs, wherein the beam combines the second beam with the first beam after the second beam has passed through a time delay loop.

The laser generator of any of the preceding paragraphs, wherein the time delay loop comprises a plurality of mirrors.

The laser generator of any of the preceding paragraphs, wherein the time delay loop comprises a mixing fiber.

The laser generator of any of the preceding paragraphs, wherein the mixing fiber is a coherence mixing fiber.

The present disclosure also includes a method of using the laser generator of any of the preceding paragraphs, wherein the method comprises coupling the laser generator to a catheter having a plurality of optical fibers and inserting the catheter into a patient's vasculature and removing at least a portion an occlusion with the patient's vasculature.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of dements, such as X1-Xn, Y1-Ym, and Z1-Zo, the phrase is intended to refer to a single dement selected from X, Y, and Z, a combination of elements selected from the same class (e.g., X1 and X2) as well as a combination of dements selected from two or more classes (e.g., Y1 and Zo).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The following documents are hereby incorporated by reference: (1) U.S. Pat. No. 5,315,614; (2) U.S. Pat. No. 7,050,692; and (3) U.S. Pat. No. 8,059,274; (4) the References listed on the last page of Exhibit 1, including but not limited to (a) Tianheng Wang, Patrick D. Kumavor, and Quing Zhu. Application of laser pulse stretching scheme for efficiently delivering laser energy in photoacoustic imaging, Journal of Biomedical Optics 17(6), 061218-1 to 061218-8 (June 2012); (b) Rajeev Khare and Paritosh K. Shukla, Ch. 10—Temporal Stretching of Laser Pulses, Coherence and Ultrashort Pulse Laser Emission, Coherence and Uitrashort Pulse Laser Emission (November 2010); and (c) Amir Herzog, Dror Malka, Zeev Zalevsky, and Amiel A. Ishaaya, Effect of spatial coherence on damage occurrence in multimode optical fibers, p. 415, Feb. 1, 2015/Vol. 40, No. 3/OPTICS LETTERS.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings are incorporated into and form a part of the specification to illustrate several examples of the present disclosure. These drawings, together with the description, explain the principles of the disclosure. The drawings simply illustrate possible and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

Figure 1:
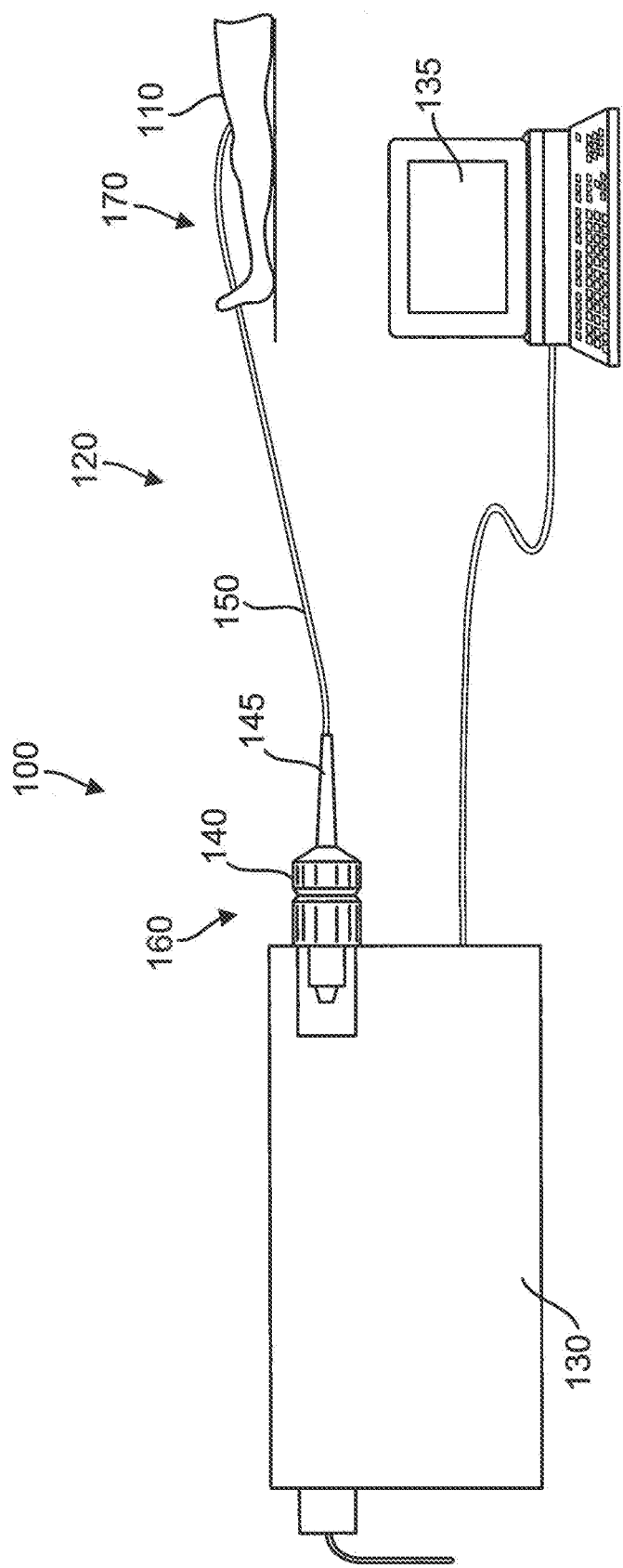
FIG. 1 illustrates an exemplary ablation system, including a laser generator and a laser catheter of the present disclosure.

Referring to FIG. 1, there is depicted an exemplary ablation system 100 of the present disclosure. Ablation system 100 includes a laser apparatus 130 coupled to a laser controller 135. Controller 135 includes one or more computing devices programmed to control laser 130. Controller 135 may be internal or external to laser apparatus 130, such as a laser generator. Laser apparatus 130 may include an excimer laser, a Nd:YAG laser or another suitable laser. In some embodiments, laser 130 produces light in the ultraviolet frequency range. In one embodiment, laser 130 produces optical energy in pulses.

Laser 130 is connected with the proximal end of a laser energy delivery system 120, illustratively a laser catheter 150 via coupler 140. Laser catheter 150 includes one or more transport members which receive laser energy from laser 130 and transports the received laser energy from a first, proximal end 160 of laser energy catheter 150 towards a second, distal end 170 of laser catheter 150. The distal end 170 of catheter 150 may be inserted into a vessel or tissue of a human body 110. In some embodiments, system 100 employs a plurality of light guides as the transport members, such as optical fibers, that guide laser light from laser 130 through catheter 150 toward a target area in human body 110.

Exemplary laser catheter devices or assemblies may include laser catheters and/or laser sheaths. Examples of laser catheters or laser sheath are sold by The Spectranetics Corporation under the tradenames ELCA™ and Turbo Elite™ (each of which is used for coronary intervention or peripheral intervention, respectively, such as recanulizing occluded arteries, changing lesion morphology, and facilitating stent placement) and SLSII™ and GlideLight™ (which is used for surgically implanted lead removal). The working (distal) end of a laser catheter typically has a plurality of laser emitters that emit energy and ablate the targeted tissue. The opposite (proximal) end of a laser catheter typically has a fiber optic coupler 140 and an optional strain-relief member 145. The fiber optic coupler 140 connects to a laser system or generator 130. One such example of a laser system is the CVX-300 Excimer Laser System, which is also sold by the Spectranetics Corporation.

The laser controller 135 of FIG. 1 includes a non-transitory computer-readable medium (for example, memory), which includes instructions and/or logic that, when executed, cause one or more processors to control laser 130 and/or other components of the ablation system 100. Controller 135 includes one or more input devices to receive input from an operator. Exemplary input devices include keys, buttons, touch screens, dials, switches, mouse, and trackballs which providing user control of laser 130. Controller 135 further includes one or more output devices to provide feedback or information to an operator. Exemplary output devices include a display, lights, audio devices which provide user feedback or information.

A laser source of laser 130 is operatively coupled to laser controller 135. Laser source is operative to generate a laser signal or beam and provide the laser signal through a fiber optic bundle of catheter 150 to the human. Fiber optic bundle serves as delivery devices for delivering the laser signal to the target area of the human body 110.

FIG. 1 depicts the catheter 150 entering the leg, preferably through the femoral artery, of the human body. As discussed above, it may be desirable to treat either cardiac arterial disease (CAD) or peripheral arterial disease (PAD). After entering the femoral artery, if the catheter 150 is intended to treat CAD, the catheter 150 will be directed through the patient's vasculature system and to the coronary arteries. Alternatively, if the catheter 150 is intended to treat PAD, the catheter 150 will be directed through the patient's vasculature system and to the peripheral arteries, such as the vasculature below the knee, particularly the vasculature in the patient's legs and/or feet.

Figure 2A:
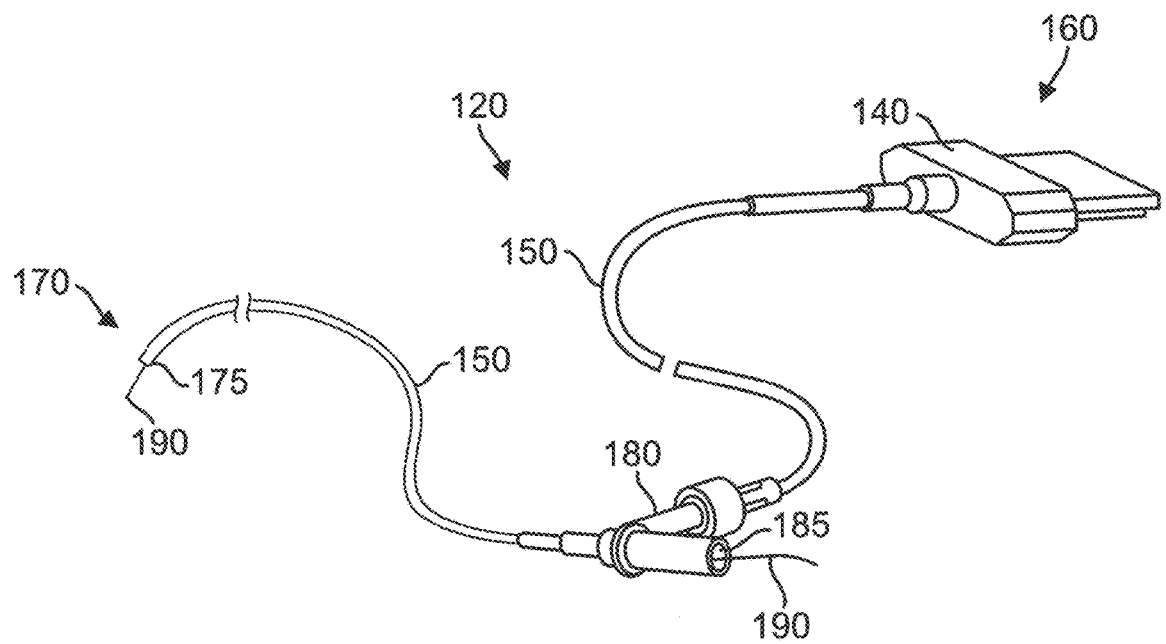
FIG. 2A is a perspective view of a laser catheter or fiber optic catheter of the present disclosure.

FIG. 2A depicts a non-limiting example of a laser energy delivery system 120, illustratively a laser catheter 150 via coupler 140, which is suitable for coupling to laser generator 130. For example, laser catheter 150 includes a proximal end 160 and a distal end 170. The catheter coupler 140 is disposed at catheter proximal end 160. Catheter coupler 140 includes a plurality of optical fibers 205, which may be arranged in one or more sets of optical fibers 205, wherein the optical fibers 205 are disposed throughout the length of the laser catheter 150, including being housed within coupler 140 and exposed at the distal tip 175 of the distal end 170. Laser catheter 150 may also include a T or Y connector 180, wherein the connector 180 has an entry port 185 for a guidewire 190 to be inserted therein. The laser catheter 150 may further include a lumen extending from the connector 180 to the distal end 170 of catheter 150 at distal tip 175, thereby allowing the guidewire 190 to be inserted through the catheter 150.

Figure 2B:
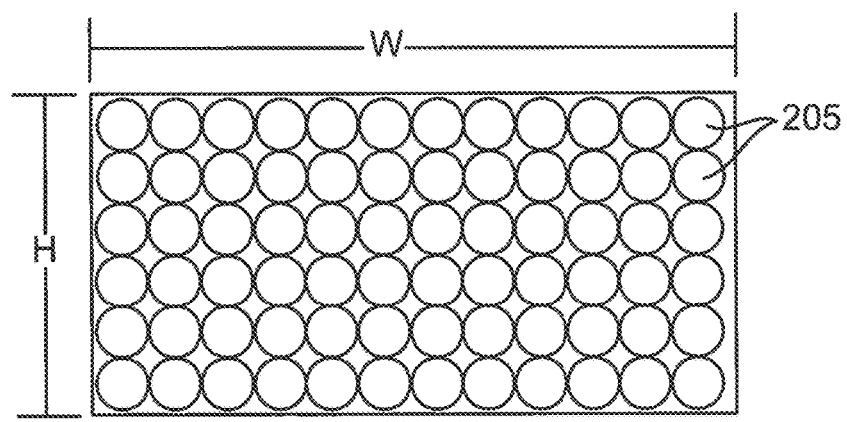
FIG. 2B is a cross sectional view of the optical fibers of the rectangular fiber coupler.

Referring to FIG. 2B, there is shown is a cross sectional view of a bundle of a plurality optical fibers 205 of a rectangular fiber coupler 140, particularly the proximal end of the coupler 140. The cross section of the coupler 140 in this figure is depicted as being rectangular, wherein the rectangular shape has a width (W) and a height (H) to match the aspect ratio different of the beam entering the coupler 140. The width (W) and a height (H) may be different than that shown in this figure, such as a smaller or larger width and/or a smaller or larger height to match the aspect ratio different of the beam entering the coupler 140. Although the cross section of the bundle of fibers is depicted as being rectangular, the cross section of the bundle of fibers may be square, triangular, circular or some other shape.

Figure 4:
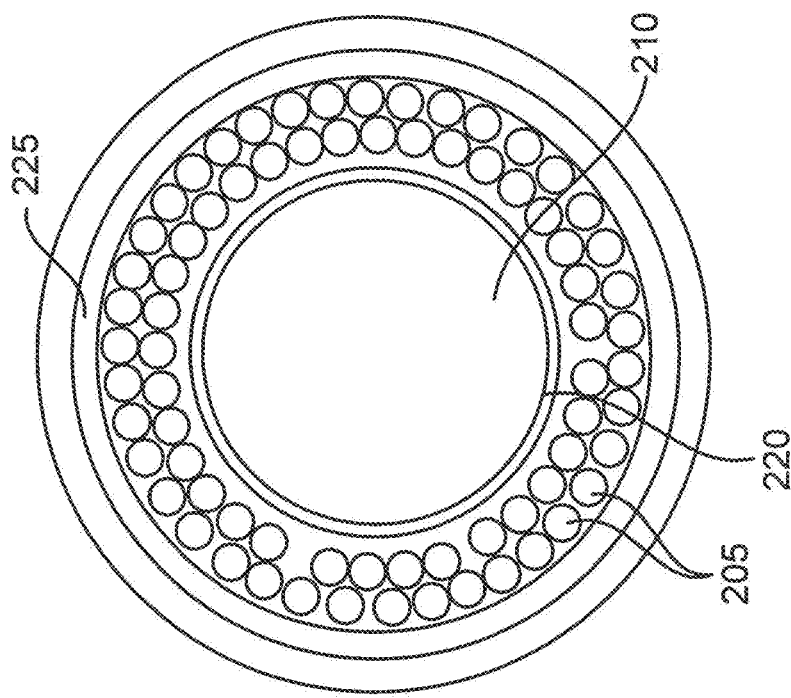
FIG. 4 is an end view of the distal end of a laser catheter or fiber optic catheter of the present disclosure.
Figure 3:
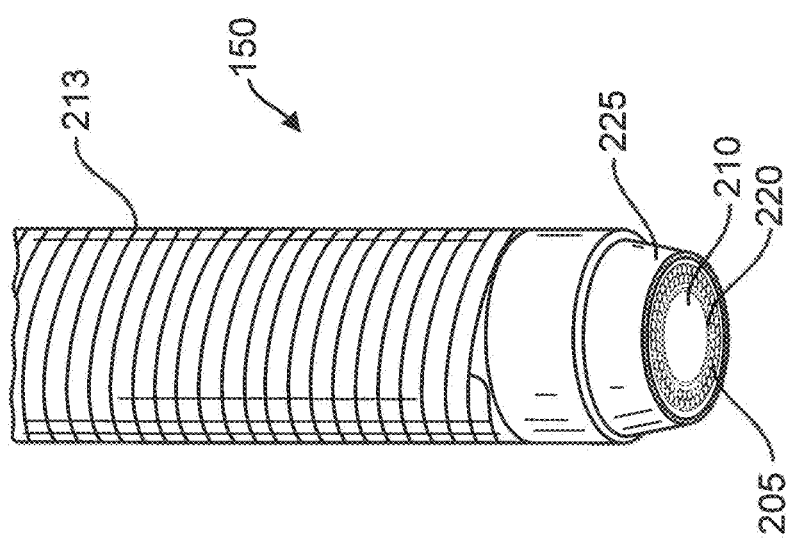
FIG. 3 is a perspective view of the distal portion of a laser catheter or fiber optic catheter of the present disclosure.

Referring now to FIG. 3 and FIG. 4, a distal end of a laser catheter 150 for an atherectomy procedure in accordance with the present disclosure is shown. The laser catheter 150 may (as depicted in FIGS. 3 and 4) or may not include a lumen 210. If a lumen 210 is included in the laser catheter 150, a clinician may slide the laser catheter over a guidewire (not shown) through lumen 210. It may, however, be preferable for the laser catheter to have a separate guidewire lumen located between the inner band 220 and outer jacket 215.

As shown, the catheter 150 comprises an outer jacket 215 or sleeve. The outer jacket 215 comprises a flexible assembly with the ability to resist user-applied forces such as torque, tension, and compression. The proximal end (not shown) of the laser catheter 150 is attached to a fiber optic coupler (not shown and discussed above). The distal end of the laser catheter 150 comprises a tapered outer band 225, which is attached to the distal end of the outer jacket 215, a plurality of optical fibers 205 acting as laser emitters, an inner band 220 creating an orifice that provides an entrance to an inner lumen 210. The energy emitted by the optical fibers 205 cuts, separates, and/or ablates the scar tissue, plaque build-up, calcium deposits and other types of undesirable lesion or bodily material within the subject's vascular system in a pattern substantially similar to that of the cross sectional configuration of the laser emitters 10.

In this particular example, the optical fibers 205 are provided in a generally concentric configuration. As the energy emitted by the optical fibers 205 contacts the undesirable bodily material within the subject's vascular system, it separates and cuts such material in a generally concentric configuration. Although FIGS. 3 and 4 illustrate the optical fibers 205 in a generally concentric configuration, those skilled in the art will appreciate that there are numerous other ways and configurations in which to arrange a plurality of laser emitters. Accordingly. FIGS. 3 and 4 are not intended to represent the only way that the distal end of a laser catheter 150 may be configured.

Figure 5:
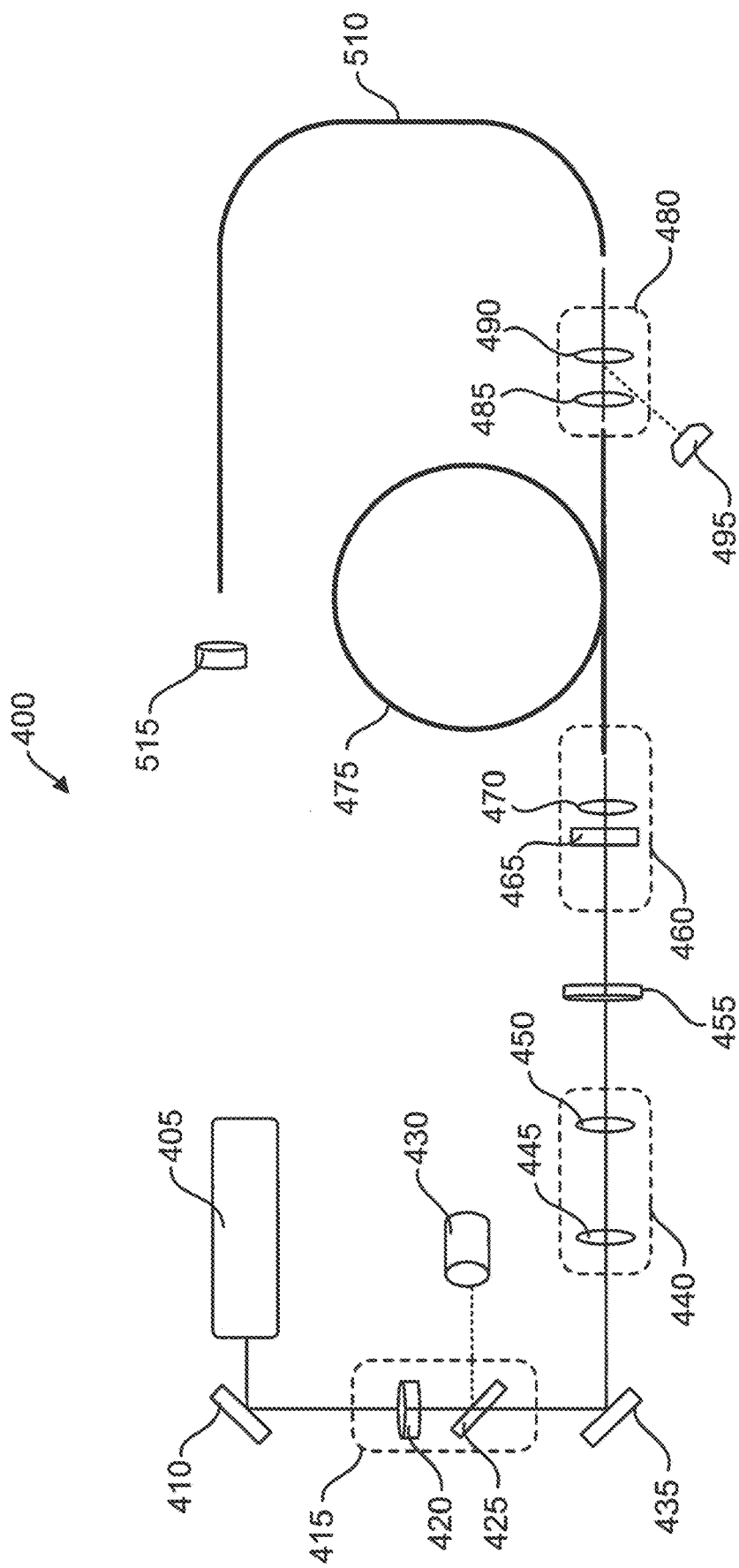
FIG. 5 is a schematic view of an ablation system of the present disclosure.

Referring to FIG. 5, there is shown an ablation system 400 of the present disclosure that includes a means for coherence mixing. Coherence mixing is a method for reducing spatial coherence damage in optical fibers used in transmitting relatively short pulsed width light, such as 355 nanometers. An example of a laser 405 that produces relatively short pulsed width light includes a Quantel DRL laser (Quantel Inc. Bozeman, Mont.), having a wavelength of 355 nanometers (nm), a pulse width of 8 nano seconds (nsec), a repetition rate of 1 to 30 Hertz (Hz) and a maximum energy output of 140 milli-joules (mJ). An alternate example of a laser 405 includes the Spectranetics Corporation's CVX-300 Excimer Laser System having a wavelength of 308 nanometers (nm), a pulse width of 135 nano seconds (nsec), a repetition rate of 1 to 80 Hertz (Hz) and a maximum energy output of about 200 milli-joules (mJ).

As discussed above, the optical fibers 205 in the laser catheter 150 that are used to deliver the energy are potentially subject to failure if the amount of energy in a pulse exceeds a certain threshold. The likelihood of such failure is increased if the laser beam inherently has a greater peak power. For example, due to the relatively short duration (e.g., 8 nsec) of the pulse width of the 355 nanometer laser beam in comparison to the 308 nanometer laser beam, which has a pulse width of 135 nsec, the 355 nanometer laser beam must have a substantially higher peak power for a given pulse because the pulse width of the 355 nanometer beam is over sixteen times shorter than the length of the pulse width of the 308 nanometer beam. Accordingly, there is a need to increase the pulse width of a laser beam in order to decrease the peak power of the energy traveling through the optical fibers in order to prevent the power level from exceeding the damage threshold of the fiber optic delivery device.

Continuing to refer to FIG. 5, laser light energy is emitted from laser 405 and into a single optical fiber 520 (or fiber optic bundle). For example, the laser light may include a wavelength of 355 nm as discussed above. After exiting the laser 405, the laser light may be deflected by a mirror 410, which directs the laser light to an energy control system 415. The energy control system 415 controls the amount of or intensity of energy entering the ablation system 400 after the laser light departs the laser 405. For example, the energy control system 415 may decrease the level of energy. The energy control system 415 may include a waveplate 420 and a thin film polarizer 425. The waveplate 420 is an optical device that alters the polarization state of a light travelling through it. One type of waveplate is a half-wave plate, which shifts the polarization direction of linearly polarized light. The half-wave plate may be mounted in a manual or motorized rotational mount, and may be disposed prior to the thin film polarizer 425 relative to the laser light's travel path. The energy control system 415, such as the waveplate 420 and thin film polarizer 425, therefore, reduces the energy level(s) of the light during component and fiber input alignment, as well as the output of the delivery fiber and/or catheter 150. The light that passes through the waveplate 420 and subsequently reflected by the thin film polarizer 425 is directed into a beam dump 430, which is an optical element used to absorb a beam of light.

As shown in FIG. 5, thin film polarizer 425 reflects a portion of the light to the beam dump 430 and the remaining portion of the light to the mirror 435. As such, after the light passes through the energy control system 415, the beam of light may be deflected by a mirror 435 and subsequently expanded by a beam expander 440. The beam expander 440 may aid in reducing the energy density of the laser light that is incident on the optics further downstream in system's optical path. Reducing the energy density of the laser light assists in preventing the light from exceeding the optical components' threshold damage levels, thereby increasing the useful life of the optical components. For example, the beam expander 440 may expand the size of the beam of light by 2.5 times or other increment, such as 1.5, 2.0, 3.0, 3.5, 4.0, 4.5, 5.0, 5.5, 6.0, 6.5 times, etc. or any sub-increment there between. One type of beam expander 440 may include a Keplerian telescope, which includes two optical lenses 445, 450.

After exiting the beam expander 440, the light beam then passes through a shutter 455 followed by a diffuser-lens assembly 460. The shutter 455 is used to switch (on/off) the light entering or not entering into the downstream optical system. The diffuser-lens assembly 460 may include an engineered diffuser 465, such as a diffractive optical element (DOE), and a lens 470 downstream of the diffuser 465. The engineered diffuser 465 will preferably be designed and/or selected such that the shape of the beam exiting the engineered diffuser 465 will resemble the shape of the mixing fiber 475 and/or the delivery fiber 510. For example, if it is desirable for the shape of the beam exiting the engineered diffuser 465 to be round, then it may desirable to use P.N.: RH-217-U-Y-A manufactured by Holo/Or Ltd. 13B Einstein Street, Science Park, Ness Ziona, 7403617 Israel because this engineered diffuser outputs a round beam. The specifications for this diffuser are as follows:

| Input Parameters | |
|---|---|
| Wavelength [nm] | 355 |
| Minimum Beam Diameter [mm] | >6 |
| Beam Mode (SM/MM) | SM or MM |
| Element Parameters | |
| Element Type | Window |
| Material | Fused Silica |
| Diameter (D) [mm] | 25.4 |
| Clear Aperture [mm] | 22.9 |
| Thickness (CT) [mm] | 3 |
| Coating | AR/AR coating |
| Output Parameters & Estimated Performance | |
| Output Shape | Round |
| Diffusion angle (full) [deg] | 0.67 |
| Transmission efficiency [%] | Close to 100% |
| Overall Efficiency [%] | ~70 |
| Remarks | High Homogeneity |

As an alternative example, if it is desirable for the shape of the beam exiting the engineered diffuser 465 to be square, then it may desirable to use P.N.: HM-271-U-Y-A manufactured by Holo/Or Ltd. 136 Einstein Street, Science Park, Ness Ziona, 7403617 Israel because this engineered diffuser outputs a square beam. The specifications for this diffuser are as follows:

| Input Parameters | |
|---|---|
| Wavelength [nm] | Wavelength [nm] 355 |
| Minimum Beam Diameter [mm] | Minimum Beam Diameter [mm] >5 |
| Beam Mode (SM/MM) | Beam Mode (SM/MM) SM or MM |
| Element Parameters | |
| Element Type | Window |
| Material | Fused Silica |
| Diameter (D) [mm] | 25.4 |
| Clear Aperture [mm] | 22.8 |
| Thickness (CT) [mm] | 3 |
| Coating | AR/AR coating |
| Output Parameters & Estimated Performance | |
| Output Shape | Square |
| Diffusion angle (full) [deg] | 0.67 × 0.67 |
| Transmission efficiency [%] | Close to 100% |
| Overall Efficiency [%] | ~76 |
| Remarks | |

As mentioned above, the diffuser-lens assembly 460 may include an engineered diffuser 465, such as a diffractive optical element (DOE), and a lens 470 downstream of the diffuser 465. The lens 470 may be a 100 mm focal length lens producing a 1.17 mm spot, which is focused incident on the input face of the coherence mixing fiber 475. The coherence mixing fiber 475 allows the typically coherent laser light entering the fiber to become out of phase due to the mixing fiber's relatively long length and large diameter, thereby emitting light portions of which are time delayed with respect to other portions. A photon of light that enters the fiber and follows the shortest path possible down the center of the fiber has a much shorter path length than a photon that enters the fiber at a steeper angle and continuously bounces off of the interior walls of this fiber. Due to the different angles of the photons entering the fiber and the length of the fiber, the coherence of the laser light is mixed and/or scrambled at the output end, thereby creating a resulting beam of light that is less coherent than that entering the mixing fiber. When this less coherent light is launched into the smaller delivery fibers the ability of the light to achieve constructive interference is greatly reduced. The coherence mixing fiber 475 may be a 1.5 mm core diameter by 1.5 meter long, fused silica multimode fiber. The light exiting the mixing fiber 475 is collimated using collimator 480, which may include two focal length lenses 485, 490. For example, lens 485 may be a 75 mm focal length lens, and lens 490 may be a 25 mm focal length lens.

The pulse widths of the beam entering and/or exiting the diffuser-lens assembly 460 were measured using a pulse detector 465, such as Thoriabs DET10A photo diode (Thorlabs, Newton, N.J.). The pulse detector 465 also triggered an oscilloscope for counting pulses during tissue ablation experiments. The beam exiting the diffuser-lens assembly 460 enters the delivery fiber 510, and is measured by an energy detector 495. An example of an energy detector 495 is a Genter Maestro energy meter (Gentec-EO, Lake Oswego, Oreg.). An example of a deliver fiber 510 includes a UV grade fused silica core and cladding with a polyimide buffer coating, wherein the fiber has a 1.1 to 1 core cladding ratio and a 0.22 numerical aperture (Polymicro Technologies, Phoenix, Ariz.). Although the delivery fiber 510 in FIG. 5 is described as a single fiber, the delivery fiber 510 may alternatively be a bundle of fibers 205 in a laser catheter 150 as described in relationship to FIGS. 1, 2A, 2B, 3 and 4 above.

Coherence Mixing Example

Using the ablation system 400 in FIG. 5, including the use of the coherence mixing method created by the incorporation of the coherence mixing fiber 475 into such system, energy output of up to 42 mJ corresponding to fluencies of 150 mJ/mm$^2$ at 20 Hz were consistently achieved through the 600 μm core diameter fiber. Coupling efficiencies from the laser output to the 600 μm optical fiber were approximately 30%. The 150 mJ/mm$^2$ out of the fiber reported in these results were limited by the 140 mJ laser output. This transmission testing was repeated 5 times with a duration of 5 minutes each run and resulted in 0 fiber failures. That is, the fiber did not break or become damaged due to light exceeding the damage threshold of the fused silica material with which fibers are constructed.

Figure 6:
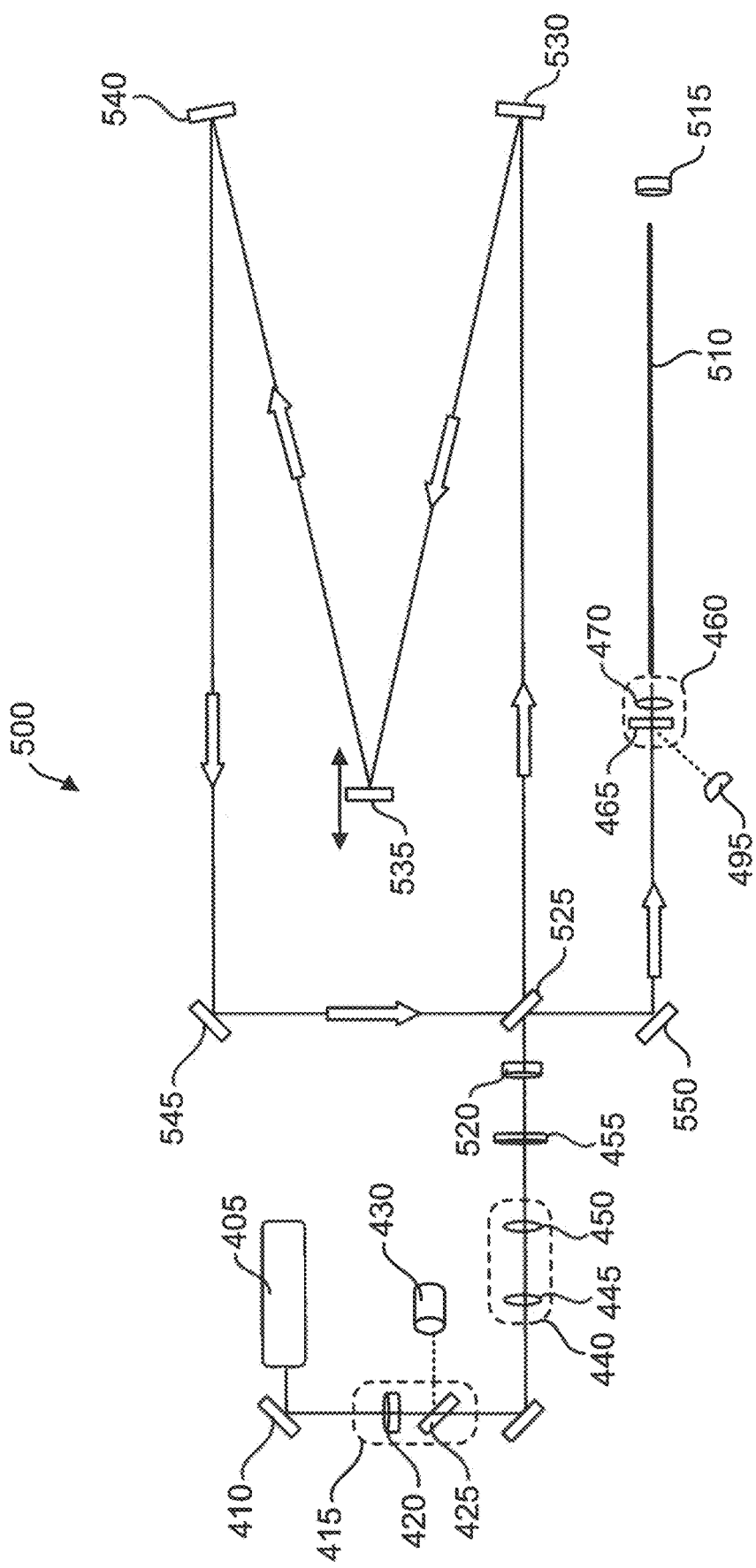
FIG. 6 is a schematic view of an alternative ablation system of the present disclosure.

Referring to FIG. 6, there is shown an ablation system 500 of the present disclosure that includes a means for stretching the pulse width of the beam. By stretching the width of a pulse of the original laser beam and creating a resulting laser beam, the peak power of the resulting light pulse(s) can be reduced relative to the peak power of the original light pulse, while maintaining the overall energy contained in the original pulse. Also, by lowering the peak power of the original pulse, higher energy levels can be transmitted through the optical fibers. The means for stretching the pulse width of the beam includes the use of optical components to split one beam into two beams, transmit one of the split beams through an optical delay loop, and re-combine the split beams into a resulting beam.

Continuing to refer to FIG. 6, the ablation system 500 is similar to the ablation system 400 in FIG. 5 in that the optical components upstream of the waveplate 520 in FIG. 6 are the same as the optical components upstream of the diffuser-lens assembly 460 in FIG. 5. For the purpose of brevity, those optical components will not be discussed again with respect to FIG. 6. The ablation system 500 in FIG. 6 includes a waveplate 520 between the shutter 455 and the beam sputter 525. By rotating this waveplate 455, the transmission and/or reflective characteristics of the split beams exiting the beam splitter 525 can be adjusted, such as the energy intensity of the split beams and the ratios of the split beams, thereby allowing modification of the height or amplitude of the pulses 705 and 710 in FIGS. 7A and 7B such that the amplitudes of the pulses are the same or similar. Accordingly, the resulting pulse 715 has an effective width with a more relatively consistent and similar amplitude.

The means for stretching the pulse width of the beam may include a beam splitter 525 and a series of mirrors 530, 535, 540, 545. The series of mirrors is designed to create an optical path that forces the beam in the optical delay loop to travel a certain distance in order to create a predetermined time delay. For example, a 120 inch optical path length may create a predetermined time delay of about 10 nsec. A longer optical path length will create a longer time delay, and a shorter optical path length will create a shorter time delay. The present disclosure contemplates using other optical path lengths to produce time delays other than 10 nsec. One way of adjusting the optical path length and the time delay includes moving one or all of the mirrors 530, 535, 540, 545. Although all of the mirrors 530, 535, 540, 545 may be fixed or moveable, FIG. 6 illustrates an example of mirror 535, which is capable of translating axially, thereby allowing for adjustment(s) of the length of the optical delay path and corresponding distance between the peaks of the pulses.

The optical delay loop begins with a beam splitter 525, which divides the original beam entering the beam splitter 525 into two beams: one of the two beams travels through the optical delay loop; and the other of the two beams does not enter the delay loop and is directed to mirror 550 and collimator 480. After the beam that travels through the delay loop travels there through, the beam sputter 525 reunites the beam that travels through the delay loop with the beam that did not enter the delay loop, thereby creating a resulting beam. And when the beam spatter 525 reunites these two spat beams, the resulting beam will comprise the same amount of energy as the original beam entering the beam splitter 525, but the peak power of the resulting beam will be substantially reduced (e.g., less than half the peak power of the original beam). The peak power of the resulting beam is substantially reduced in comparison to the original beam entering the beam splitter 525 because the optical delay loop causes the beam that traveled through the delay loop to overlaps with the portion of the beam that originally did not enter the optical delay loop at a predetermined time, such that the peak energy levels of the two portions are offset by such predetermined time, thereby creating a resulting beam that appears to have a longer pulse width because the peak energy levels of the two split beams are adjacent one another and appear, in combination, to be a single peak for a longer duration of time.

Figure 7B:
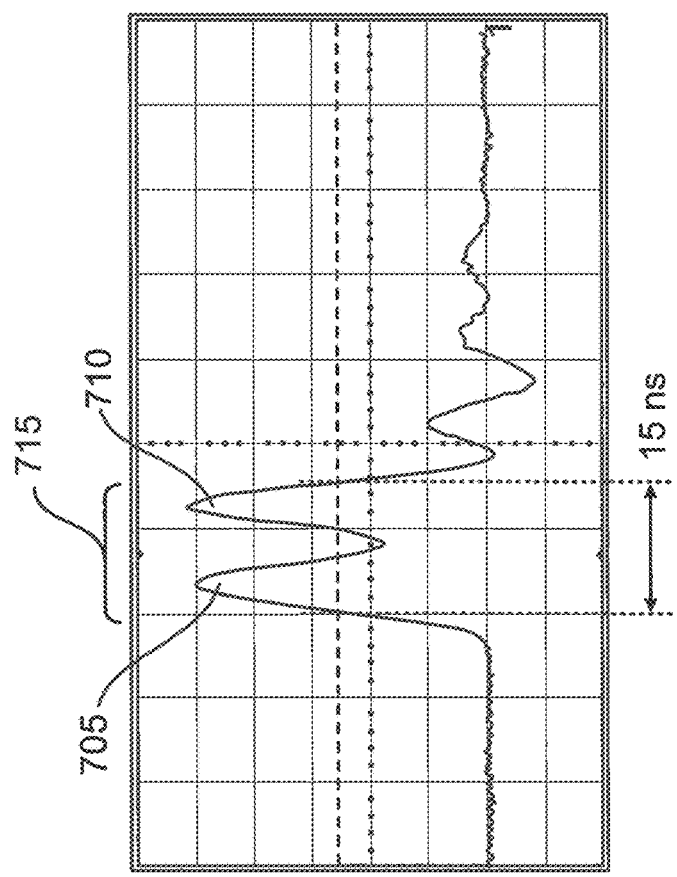
FIG. 7B is an illustration of an energy signal emitted from the ablation system depicted in FIG. 6, wherein the energy signal is a resulting signal formed by combining and overlapping about 40 percent of the energy originally entering the beam splitter and the remaining energy that travels through a time-delay loop.
Figure 7A:
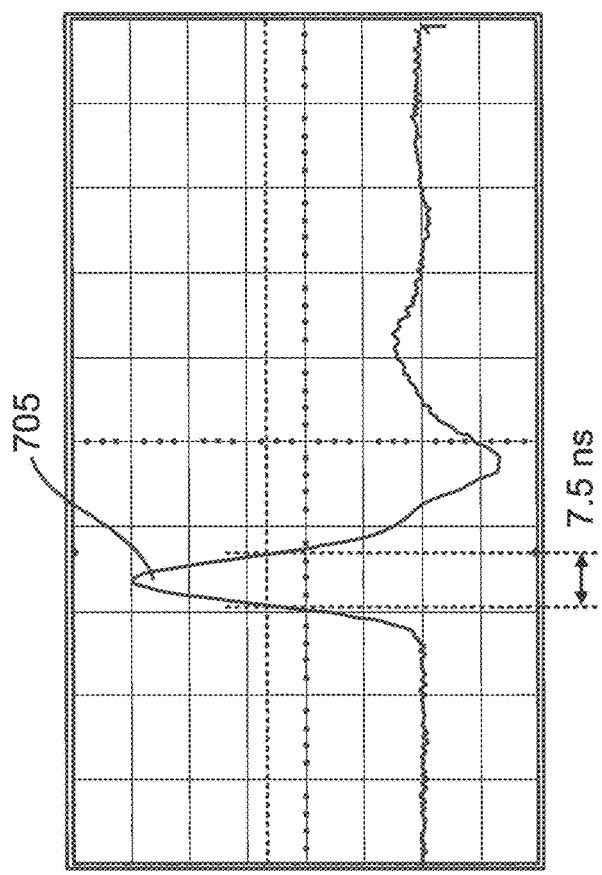
FIG. 7A is an illustration of an energy signal emitted from the ablation system depicted in FIG. 6, wherein the energy signal is about 40 percent of the energy originally entering the beam splitter.

Referring to FIG. 7A, there is depicted an energy signal emanating from the beam splitter 525 toward the mirror 550 in the ablation system depicted in FIG. 6. Assuming the beam splitter 525 is a 40/60 beam splitter, the beam splitter 525 receives the original beam from the waveplate 520 and splits the original beam into two beams, wherein one beam having about 40 percent of the energy originally entering the beam splitter 525, does not travel through the optical delay loop and is directed to the mirror 550, and the other split beam has about 60 percent of the energy originally entering the beam splitter 525 and travels through the optical delay loop. This energy signal 705 in FIG. 7A is representative of the split beam that does not travel through the optical delay loop, and this beam has a pulse width of about 7.5 nanoseconds (nsec). Accordingly, the original beam entering the beam splitter 525 would have a peak power of about 2.5 times greater than that shown in FIG. 7A, but the pulse width of the original energy signal would still be about 7.5 nsec. As such the amount of energy produced by the signal in FIG. 7A is about 40 percent of the amount of energy of the original signal entering the beam splitter 525. Accordingly, 60 percent of the amount of energy entering the beam splitter 525 is in the split beam entering the time delay loop. Although a 40/60 beam splitter is discussed, the scope of the present disclosure includes other beam splitters having other ratios, such as 5/95, 10/90, 15/85, 20/80, 25/75, 30/70, 35/65, 45/55, 50/50, 55/45, 60/40, 65/35, 70/30, 75/25, 80/20, 85/15, 90/10, 95/5 and any other ratio(s). Also, the beam spatter receiving the original beam can spat the original beam into two beams, and one beam that travels through the optical delay loop can have any percentage of the energy originally entering the beam splitter, and the other split beam can have the remaining percentage of energy and not travel through the optical delay loop. Using other ratios of beam splitters will adjust the peak energy of the resulting signal.

Referring to FIG. 7B, there is shown a resulting energy signal emitted from the ablation system depicted in FIG. 6, wherein the resulting energy signal is a combination of the split beam that did not enter the time delay loop and has about 40 percent of the energy originally entering the beam splitter 525 and the split beam that entered the time delay loop which contains the remaining energy that traveled through the time delay loop. As shown in FIG. 7B, the first peak 705 correlates to the beam or pulse that did not travel through the optical delay loop, and the second peak 710 correlates to the beam or pulse that travels through the optical delay loop. As one of skill in the art can see, the two peaks have substantially the same height, which means that each pulse has substantially the same amount of energy, and when the two pulses are combined, the resulting signal has substantially the same amount of energy that enters the beam splitter 525, but the peak energy of the resulting signal is reduced and spread over a longer duration 715 having an stretched puke width (15 ns) that is effectively twice as long as the pulse width (7.5 ns) entering the beam splitter, thereby minimizing potential damage to the delivery fiber(s) 510. Although this example illustrates stretching the width of the original pulse to a pulse width in the resulting beam to twice as long, the present disclosure encompasses stretching the width of the original pulse to other lengths, such as any increment between 1 and 10.

Referring again to FIG. 6, the ablation system 500 is similar to the ablation system 400 in FIG. 5 except the coherence mixing fiber 475 in FIG. 5 is replaced with the means for stretching the puke width of the beam, and the ablation system 500 in FIG. 6 also includes a waveplate 520 between the shutter 455 and the beam splitter 525. The means for stretching the pulse width of the beam may include a beam splitter 525 and a series of mirrors 530, 535, 540, 545. The series of mirrors is designed to create a predetermined time delay of about 10 nsec over about a 120 inch optical path length. It may also be desirable for one or more of the mirrors, such as mirror 535, to translate axially, thereby allowing for adjustment(s) of the length of the optical delay path and corresponding distance between the peaks of the pulses.

Figure 8A:
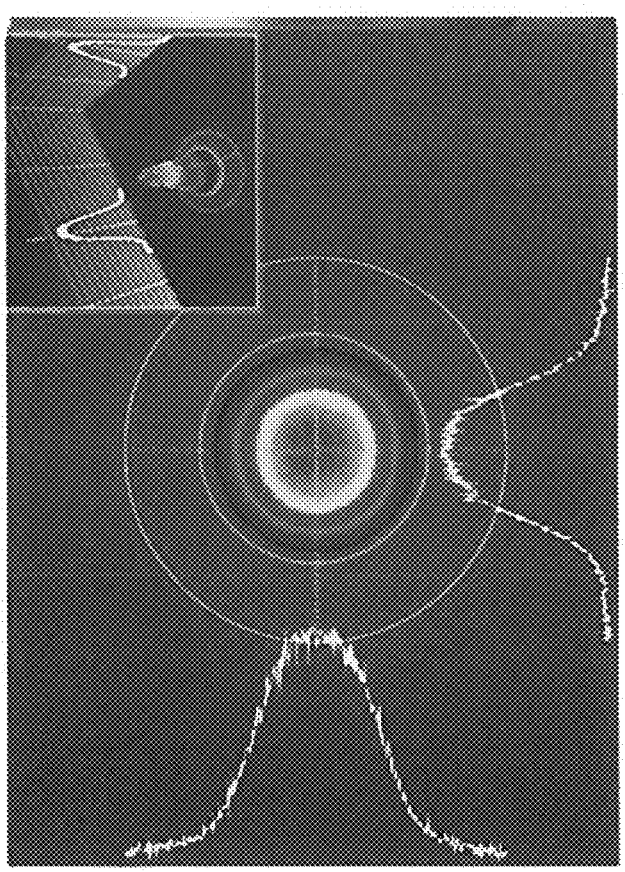
FIG. 8A is a colored illustration depicting the energy density of a laser beam emitted from the ablation system depicted in FIG. 6 using a circular shaped optical assembly.
Figure 8B:
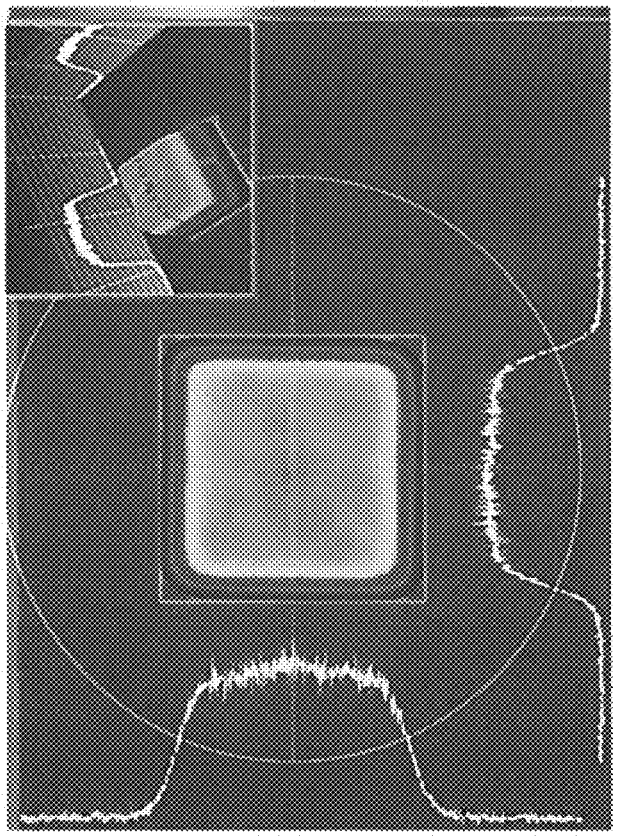
FIG. 8B is a colored illustration depicting the energy density of a laser beam emitted from the ablation system depicted in FIG. 6 using a rectangular shaped optical assembly.

As discussed above, the engineered diffuser 465 assists in focusing the beam into the desired shape, such as round or square shape. The engineered diffuser 465 is also incorporated in the ablation system 500 of FIG. 6 such that the engineered diffuser 465 is located downstream of the means for stretching the pulse width of the beam. The combination of such means and the engineered diffuser 465 allows the ablation system 500 to output a resulting beam having increased symmetry and homogeneity in comparison to a resulting beam exiting the ablation system 500 without the engineered diffuser. As depicted in FIG. 8A, the energy density of a beam produced by an engineered diffuser 465 outputting a round beam is symmetrical and relatively homogeneous, and as depicted in FIG. 8B, the energy density of a beam produced by an engineered diffuser 465 outputting a square beam is symmetrical and relatively homogeneous, Although the delivery fiber 510 in FIG. 6 may be a single fiber, the delivery fiber 510 may alternatively be a bundle of fibers 205 in a laser catheter 150 as described in relationship to FIGS. 1, 2A, 2B, 3 and 4 above.

Pulse Width Stretching Example 1

Using the pulse stretching launch method described above with a 355 nm laser, energy outputs of up to 56 mJ at 20 Hz were achieved through single 600 µm fibers. This output energy corresponds to a fluence of 200 mJ/mm$^2$. Coupling efficiencies from the laser output to the 600 µm optical fiber were in the 40% range. The fiber output energy achieved was limited by the 140 mJ laser output energy. This transmission testing was repeated 5 times with a duration of 6 minutes each run, and resulted in 0 fiber failures.

Pulse Width Stretching Example 2

Using the pulse stretching launch method described above with a 355 nm laser, 2.0 mm (97×100 µm core diameter fiber) multi-fiber catheters were tested in air at energies of 43.5 mJ corresponding to a fluence of 55 mJ/mm$^2$. Coupling efficiencies from the laser output to the multi-fiber catheter were approximately 31%. The fiber output energy achieved was limited by the total energy available using this launch method. No fiber damage at the coupler, tip, or mid-shaft of the catheter was observed. This transmission testing was repeated 5 times with a duration of 5 minutes each run and resulted in 0 fiber failures. The lack of fiber damage that was observed in section 3.2 and absent using this launch method is thought to be due to the homogenized input beam profile that is achieved with the placement of the DOE previous to the fiber coupling lens.

Tissue Ablation Example

To perform tissue ablation comparisons of 355 nm laser light to 308 nm light, fresh porcine aorta tissue was used. The tissue was sent via overnight delivery the day of harvest. It was placed in a bag with saline and stored at 15° C. until use. All tissue was tested within 5 days of harvest to limit tissue degradation prior to testing. When comparative results are presented, samples were derived from the same tissue and the testing was performed on the same day.

The porcine aorta was trimmed to produce a flat tissue sample that was consistent in thickness. This sample was then pinned to a piece of cork sheet intimal surface up. The cork sheet had a through hole that the tissue spans. The cork and tissue sample were then placed in a petri dish and submerged in saline. The petri dish was then placed on a digital scale to set and monitor the downward force of the fiber. The fiber optic was held in a teeter-totter type balance that allowed fine adjustment of the downward force applied.

A shutter in the laser beam path previous to fiber coupling was opened to allow light into the delivery fiber. The tissue was monitored as the fiber penetrated through it. When the fiber exited through the back side of the tissue, the shutter was closed and the number of pulses used for penetration was recorded. The tissue was removed after testing and the thickness was measured in the location of the ablated holes using a dial thickness gauge. The penetration per pulse was then calculated and compared.

The tissue testing was performed using a 600 µm single fiber transmitting a fluence of 60 mJ/mm$^2$ and a pulse repetition rate of 20 Hz for 355 nm and 308 nm. Typically, 60 mJ/mm$^2$ fluence output represents the energy fluence setting used by physicians that are currently using the Spectranetics CV X excimer laser. The 20 Hz pulse repetition rate was chosen to fall within the specification of the 355 nm laser being tested. Testing was conducted with 4 different downward forces applied to the fiber optic. Ten full penetration samples were collected at each downward force setting for 355 nm and 308 nm. After testing the tissue samples were photographed at 50× magnification and fixed in a 10% formalin solution.

Figure 9:
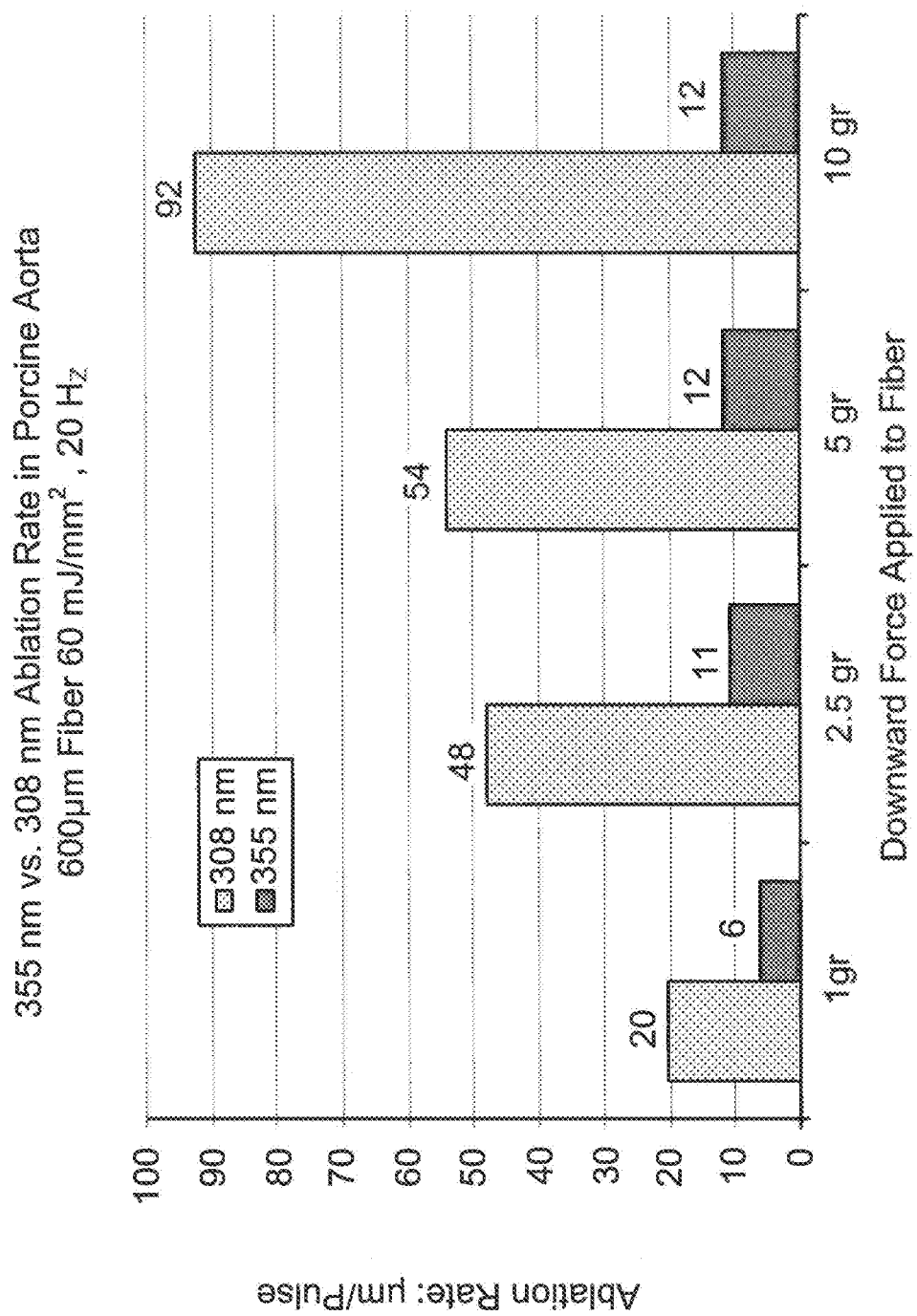
FIG. 9 is a comparison of the ablation rates emitted from a 355 nm laser system similar to or the same as that illustrated in FIG. 6, which includes a beam stretching technique, relative to a 308 nm laser system without employing a beam stretching technique.

Tissue samples were sent out to an outside lab and processed for histopathology. Slide sections for each sample were stained with hematoxylin and eosin (H&E) for light microscopy evaluation and imaging. FIG. 9 shows the comparative tissue penetration rates between 355 nm and 308 nm at different applied fiber forces using the method(s) described in the Tissue Ablation Example. The penetration of the 308 nm light was approximately 3 times faster with 1 gr of downward force and approximately 8 times faster penetration with 10 gr of downward force on the fiber. The appearance of the ablated holes is similar at 1 gr of force but smaller for 308 nm holes produced with 10 gr of downward force on the fiber. These results of testing were analyzed for penetration rates only.

During the testing, distal end fiber failures were observed 4 times out of the 40 samples during the 355 nm sample testing and 0 times out of the 40 samples during the 308 nm testing. It is believed that this fiber damage was a result of the higher peak powers of the short pulse width 355 nm laser light.

Figure 10B:
FIG. 10B is an image of holes ablated in a porcine aorta with a single 600 micron optical fiber applying a downward force of about 5 grams and using 308 nm laser system, wherein the fiber outputs about 60 mJ/mm$^2$ at 20 Hz.
Figure 10A:
FIG. 10A is an image of holes ablated in a porcine aorta with a single 600 micron optical fiber applying a downward force of about 5 grams and using 355 nm laser system similar to or the same as that illustrated in FIG. 6, wherein the fiber outputs about 60 mJ/mm$^2$ at 20 Hz.

FIG. 10A is an image of holes ablated in a porcine aorta with a single 600 micron optical fiber applying a downward force of about 5 grams and using 355 nm laser system similar to or the same as that illustrated in FIG. 6, wherein the fiber outputs about 60 mJ/mm$^2$ at 20 Hz. FIG. 10B is an image of holes ablated in a porcine aorta with a single 600 micron optical fiber applying a downward force of about 5 grams and using 308 nm laser system, wherein the fiber outputs about 60 mJ/mm$^2$ at 20 Hz. The ablated holes in FIGS. 10A and 10B have similar appearance and show no visible charring when viewed at 50× magnification.

Figure 11B:
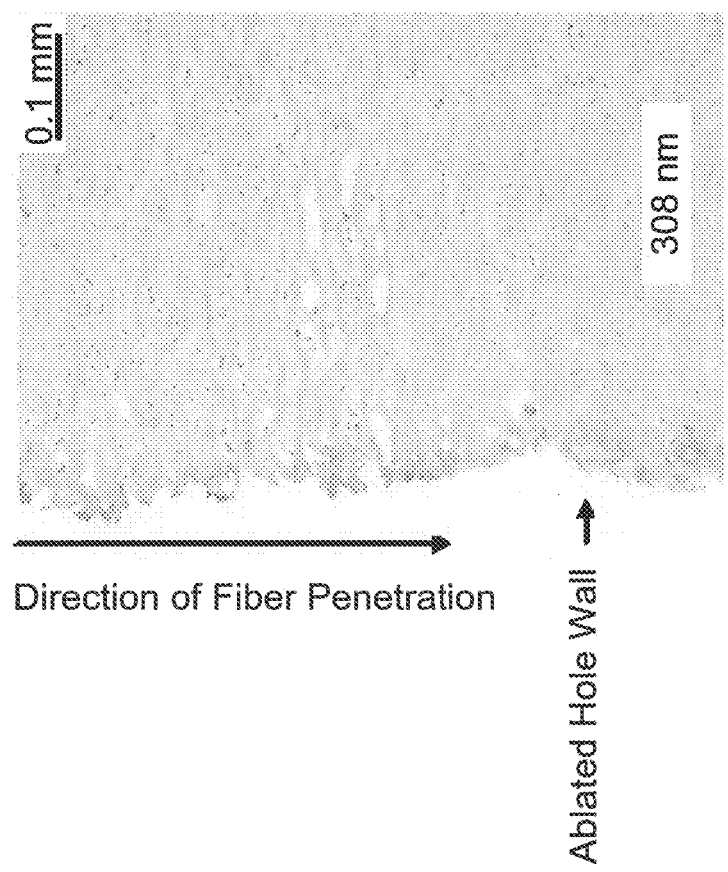
FIG. 11B is an image of a histological cross section of the holes ablated in a porcine aorta with a single 600 micron optical fiber applying a downward force of about 5 grams and using 308 nm laser system, wherein the fiber outputs about 60 mJ/mm2 at 20 Hz.
Figure 11A:
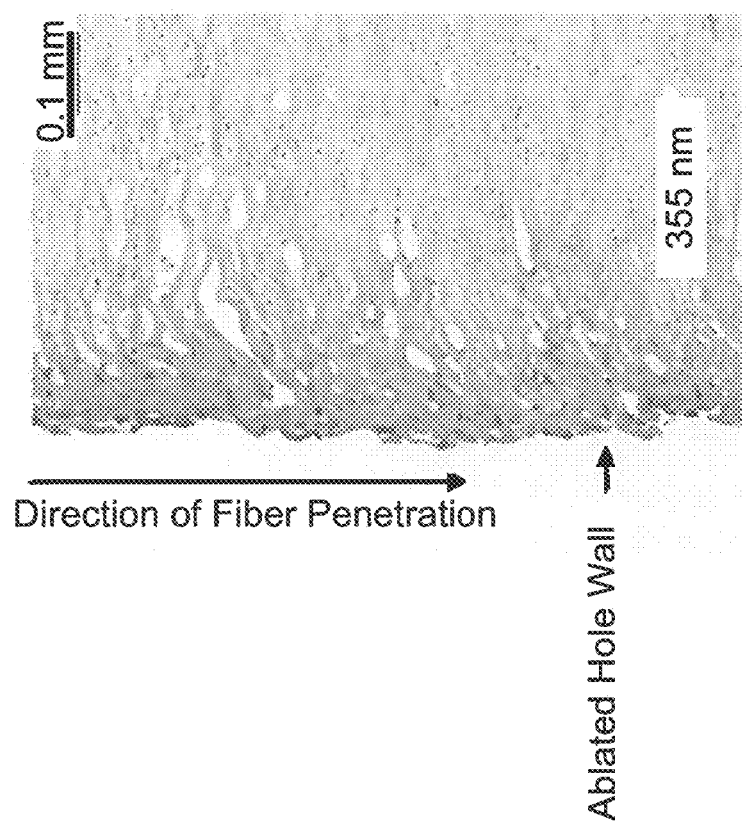
FIG. 11A is an image of a histological cross section of the holes ablated in a porcine aorta with a single 600 micron optical fiber applying a downward force of about 5 grams and using 355 nm laser system similar to or the same as that illustrated in FIG. 6, wherein the fiber outputs about 60 mJ/mm$^2$ at 20 Hz.

FIG. 11A is an image of a histological cross section of the holes ablated in a porcine aorta with a single 600 micron optical fiber applying a downward force of about 5 grams and using 355 nm laser system similar to or the same as that illustrated in FIG. 6, wherein the fiber outputs about 60 mJ/mm$^2$ at 20 Hz. FIG. 11B is an image of a histological cross section of the holes ablated in a porcine aorta with a single 600 micron optical fiber applying a downward force of about 5 grams and using 308 nm laser system, wherein the fiber outputs about 60 mJ/mm$^2$ at 20 Hz. A number of variations and modifications of the disclosure may be used. It would be possible to provide for some features of the disclosure without providing others. FIGS. 11A and 11B show that laser-produced holes were full thickness through the vessel wall with resulting localized tissue disruption and heat-generated tissue denaturation lining the defects. The fiber penetration was initiated from the intimal surface of the aorta sample.

Figure 12:
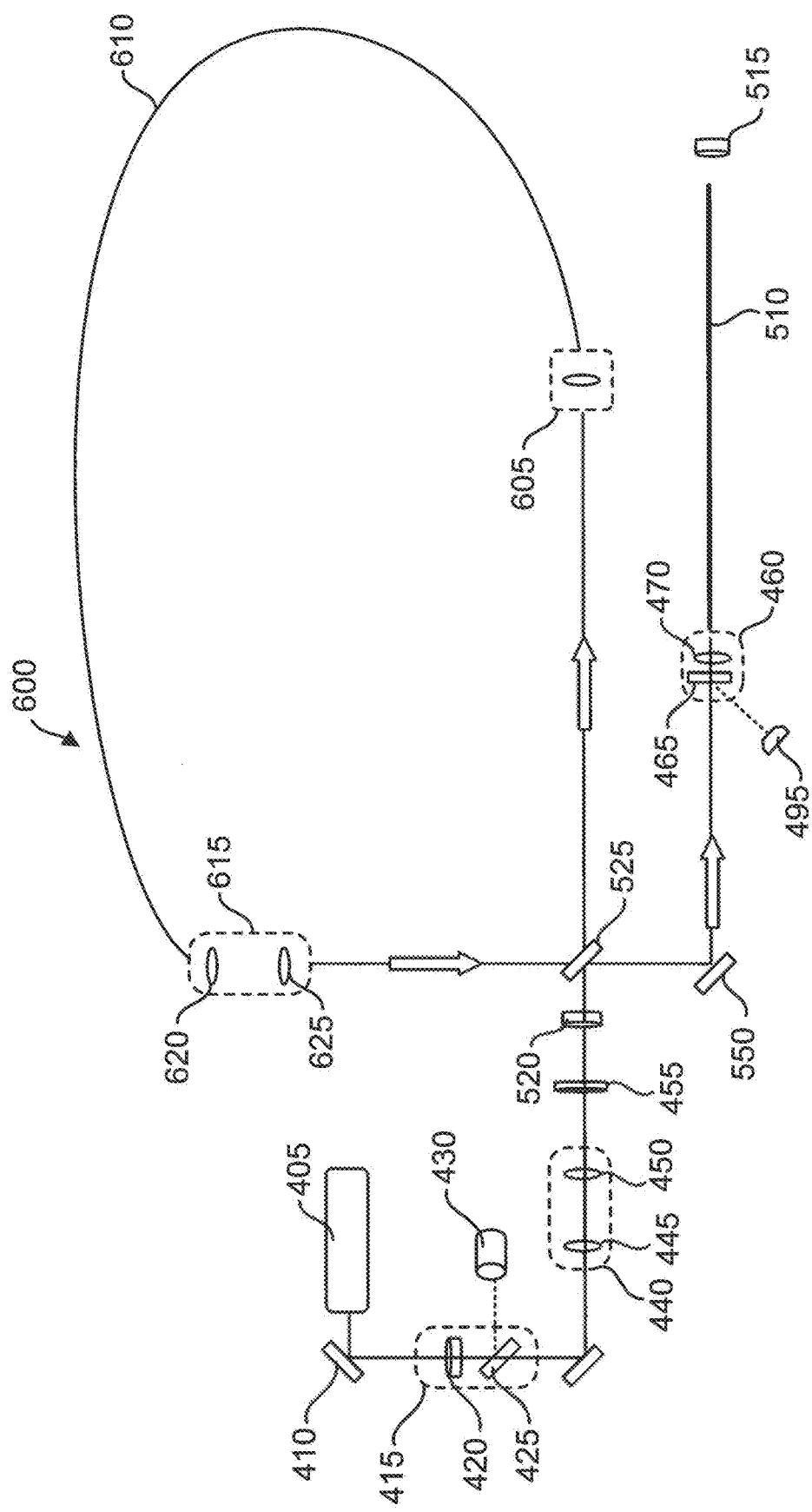
FIG. 12 is a schematic view of a further alternative ablation system of the present disclosure.

Referring to FIG. 12, there is shown a further alternative ablation system 600 of the present disclosure. The ablation system 600 of is similar to the ablation system 500 in FIG. 6 except that the means for stretching the pulse width of the beam in FIG. 12 may include a beam splitter 525 and an optical coherence mixing fiber 610 of sufficient length to cause the split beam to travel there through and create the desired predetermined time delay in lieu of using a beam splitter 525 and a series of mirrors 530, 535, 540, 545 as shown in FIG. 6. Continuing to refer to FIG. 12, it may be desirable to include a coupling lens 605 between the beam splitter 525 and the optical coherence mixing fiber 610, and it may be desirable to include a collimator 615 that includes two optical lenses 620, 625 to collimate the light as it re-enters the optical path, including the beam splitter. Incorporating the optical coherence mixing fiber 610 into the means for stretching the pulse width of the beam provides the ablation system with the advantages of reducing the peak energy of the original beam by spreading the energy over a longer duration and creating a more homogenized signal, thereby minimizing potential damage to the delivery fiber(s) 510.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A laser generator comprising:
a laser source producing a beam of light; and
an optical assembly downstream of the laser source, wherein the optical assembly receives the beam of light, wherein the optical assembly comprises:
a waveplate receiving the beam of light;
a thin film polarizer downstream of the waveplate and receiving the beam of light and reflecting a first portion of the beam and allowing a second portion of the beam to pass there through;
a beam dump receiving the first portion of the beam;
a beam expander downstream of the waveplate and receiving the second portion of the beam;
a diffuser downstream of the beam expander and receiving the second portion of the beam of light; and
a mixing fiber downstream of the diffuser and receiving the second portion of the beam of light, wherein the mixing fiber emits the second portion of the beam of light.

2. The laser generator of claim 1, wherein the beam of light comprises a wavelength of about 355 nanometers.

3. The laser generator of claim 1, wherein the beam of light comprises a wavelength between about 10 nanometers to about 5000 nanometers.

4. The laser generator of claim 1, wherein the diffuser is a diffracting optical element.

5. A laser generator comprising:
a laser source producing a beam of light having a plurality of pulses, wherein the pulses comprise a pulse width; and
an optical assembly downstream of the laser source, wherein the optical assembly receives the beam of light, wherein the optical assembly comprises:
a waveplate receiving the beam of light;
a thin film polarizer downstream of the waveplate and receiving the beam of light and reflecting a first portion of the beam and allowing a second portion of the beam to pass there through, wherein the second portion of the beam has the pulse width;
a beam dump receiving the first portion of the beam;
a means for stretching the pulse width of at least one of the plurality of pulses in the second portion of the beam; and
a diffuser downstream of the means for stretching the pulse width and receiving and emitting the other portion of the second beam.

6. The laser generator of claim 5, wherein the means for stretching the width of at least one of the plurality of pulses comprises a beam splitter and a plurality of mirrors creating a beam path.

7. The laser generator of claim 6, wherein at least one of the mirrors is capable of translating.

8. The laser generator of claim 5, wherein the means for stretching the width of at least one of the plurality of pulses comprises a beam splitter.

9. The laser generator of claim 8, wherein the beam splitter splits the second portion of the beam into a first beam and a second beam.

10. The laser generator of claim 9, wherein the beam combines the second beam with the first beam after the second beam has passed through a time delay loop.

11. The laser generator of claim 10, wherein the time delay loop comprises a plurality of mirrors.

12. The laser generator of claim 10, wherein the time delay loop comprises a mixing fiber.

13. The laser generator of claim 12, wherein the mixing fiber is a coherence mixing fiber.

14. A method of using the laser generator of claim 5, wherein the method comprises coupling the laser generator to a catheter having a plurality of optical fibers and inserting the catheter into a patient's vasculature and removing at least a portion of an occlusion within the patient's vasculature.

* * * * *